United States Patent
Butts

(10) Patent No.: US 6,451,869 B1
(45) Date of Patent: Sep. 17, 2002

(54) IRRADIATION-CURABLE SILICONE COMPOSITIONS, PHOTO-ACTIVE PLATINUM (IV) COMPOUNDS, AND METHOD

(75) Inventor: Matthew David Butts, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 169 days.

(21) Appl. No.: 09/660,965

(22) Filed: Sep. 13, 2000

Related U.S. Application Data

(62) Division of application No. 09/303,410, filed on May 3, 1999, now Pat. No. 6,150,546.

(51) Int. Cl.$^7$ .............................. C08F 2/50; C08F 4/80; C08J 3/28; C07F 17/02; C07F 7/08
(52) U.S. Cl. .............................. 522/66; 522/6; 522/63; 522/68; 522/99; 522/69; 522/148; 522/172; 522/40; 522/41; 522/44; 522/46; 522/47; 522/48; 522/52; 522/53; 427/508; 427/515; 427/517; 427/519; 428/446; 428/447; 428/452
(58) Field of Search .............................. 522/6, 63, 66, 522/68, 99, 69, 148, 172, 40, 41, 44, 46, 47, 48, 52, 53; 427/508, 515, 517, 519; 428/446, 447, 452; 442/59, 153, 157

(56) References Cited

U.S. PATENT DOCUMENTS

| | | | | |
|---|---|---|---|---|
| 4,510,094 A | | 4/1985 | Drahnak | |
| 4,530,879 A | * | 7/1985 | Drahnak | 204/157.74 |
| 4,600,484 A | | 7/1986 | Drahnak | |
| 4,770,942 A | * | 9/1988 | Itoh et al. | 427/515 |
| 4,883,569 A | * | 11/1989 | Endo et al. | 240/157.74 |
| 4,916,169 A | | 4/1990 | Boardman et al. | |
| 4,939,065 A | * | 7/1990 | Cavezzan et al. | 430/154 |
| 4,957,607 A | * | 9/1990 | Endo et al. | 204/157.74 |
| 5,070,118 A | * | 12/1991 | Eckberg | 522/148 |
| 5,145,886 A | * | 9/1992 | Oxman et al. | 522/66 |
| 5,502,084 A | * | 3/1996 | Cavezzan et al. | 522/99 |
| 5,952,397 A | * | 9/1999 | Fujiki et al. | 264/496 |
| 6,046,250 A | * | 4/2000 | Boardman et al. | 428/343 |
| 6,127,446 A | * | 10/2000 | Butts | 522/29 |
| 6,150,546 A | * | 11/2000 | Butts | 522/99 |
| 6,376,569 B1 | * | 4/2002 | Oxman et al. | 428/343 |

OTHER PUBLICATIONS ( η5 –Cyclopentadienyl)trialkylplatinum Photohydrosilylation Catalysts. Mechanism of Active Catalyst Formation and Preparation of a Novel Bis(slly1)platinum Hydride, Organometallics, 1992, 11, Larry D. Boardman—4194–4201.

"195Pt NMR Study of (η5–Cyclopentadienyl) trialkylplatinum (IV) Complexes" by Larry D. Boardman and Richard A. Newmark, Magnetic Resonance in Chemistry, vol. 30, 481–489 (1992).

"Reactions of (π–1,5 Cyclooctadiene)Orgnoplatinum(II)Compounds and the Synthesis of Perfluoroalkylplatinum Complexes" by H.C. Clark and L.E. Manzer, Journal of Organometallic Chemistry, 59 (1973) 411–428.

* cited by examiner

Primary Examiner—James J. Seidleck
Assistant Examiner—Sanza L. McClendon
(74) Attorney, Agent, or Firm—Bernadette M. Bennett; Noreen C. Johnson

(57) ABSTRACT

Cyclopentadienylplatinum (IV) compounds having $C_{7-20}$ aromatic radical substitution on the cyclopentadienyl ring have been found to impart enhanced cure speed and shelf-life stability to irradiation-curable silicone mixtures.

11 Claims, No Drawings

IRRADIATION-CURABLE SILICONE COMPOSITIONS, PHOTO-ACTIVE PLATINUM (IV) COMPOUNDS, AND METHOD

This application is a division of Ser. No. 09/303,410 filed May 3, 1999, now U.S. Pat. No. 6,150,546 issued Nov. 21, 2000.

BACKGROUND OF THE INVENTION

The present invention is directed to photo-active cyclopentadienylplatinum (IV) compounds, and to irradiation-curable silicone compositions containing such compounds as photo-active platinum (IV) catalysts.

Drahnak, U.S. Pat. No. 4,600,484, is directed to a hydrosilylation process involving the addition between silicon hydride compounds (i.e. compounds containing the Si—H moiety) and compounds containing aliphatic unsaturation. Drahnak discloses that his process is activated by actinic radiation. Drahnak uses a platinum complex having the formula, $$CpPt(R)_3, \tag{1}$$

where Cp is cyclopentadienyl and R is a $C_{1-18}$ aliphatic organic radical.

The Drahnak catalyst consists of a cyclopentadienyl group, Cp, eta-bonded to a platinum (IV) group, $Pt(CH_3)_3$, which is substituted with three sigma bond ed aliphatic radicals. It is al so reported in U.S. Pat. No. 4,600,484, that the cyclopentadienyl group Cp can be further modified with organosilyl groups.

Boardman et al., U.S. Pat. No. 4,916,169, shows a visible light-activated hydrosilylation process for effecting the addition of a silicon hydride to compounds containing aliphatic unsaturation. In accordance with the hydrosilylation practice of Boardman et al., a polycyclic aromatic organic compound, such as anthracene, is physically blended as a sensitizer with a photo-active platinum compound, such as shown by formula (1). Based on the theory of Boardman et al., the sensitizer effects a visible light energy transfer to further enhance the photo-activation of the platinum compound. While beneficial cure results are reported by Boardman et al., it has been found that the sensitizer is sometimes incompatible in the silicone curable silicone mixture and/or a large amount of sensitizer is required to be effective.

It would be desirable therefore to provide additional procedures for improving the efficiency of photo-activated platinum (IV) compounds as catalysts for effecting the cure of irradiation-curable silicone compositions.

Further, it would be desirable to provide photo-active platinum compounds comprising a cyclopentadienyl group chemically combined to a Pt (IV) group, which did not require the separate blending of an incompatible organic material, such as anthracene, into an irradiation-curable silicone mixture.

BRIEF SUMMARY OF THE INVENTION

The present invention is based on the discovery that a cyclopentadienylplatinum (IV) compound of formula (2), having a $C_{7-20}$ aromatic organic radical attached to the cyclopentadienyl is more effective as a hydrosilylation catalyst for effecting the cure of an irradiation-curable silicone mixture, than is a mixture an aromatic organic compound, for example, phenanthrene and a photo-active cyclopentadienylplatinum (IV) compound, such as shown by formula (1), which is free of aromatic substitution.

In one of its embodiments the present invention comprises platinum (IV) compounds having the formula, $$[(R^1)_a(R^2)_bCp]Pt(R^3)_3 \tag{2}$$

where $R^1$ is a $C_{7-20}$ aromatic organic radical, $R^2$ and $R^3$ are each independently a $C_{1-22}$ aliphatic organic radical, Cp is a cyclopentadienyl radical, "a" is an integer equal to 1 to 3 inclusive, "b" is an integer equal to 0 to 3 inclusive, and the sum of a+b is equal to 1 to 4 inclusive.

In another of its embodiments the present invention comprises a method for making platinum (IV) compounds of formula (2), comprising, effecting reaction between a $C_{7-20}$ aromatic substituted cyclopentadienyl species having the formula, $$(R^1)_a(R^2)_bCpM, \tag{3}$$

and a platinum (IV) compound having the formula, $$XPt(R^3)_3 \tag{4}$$

where $R^1$, $R^2$, $R^3$, Cp, "a" and "b" are as previously defined, M is a metallic anion, such as lithium, and X is an anionic leaving group, such as triflate, borate, phosphate, or halogen.

In still another of its embodiments the present invention comprises irradiation-curable silicone compositions comprising, (a) an alkenyl-substituted polydiorganosiloxane having alkenyl radicals attached to silicon by carbon-silicon bonds, where the alkenyl radicals can be in the terminal position, in the polymer backbone, or a combination thereof, (b) a silicon hydride cross-linker, and, (c) an amount of a photo-active cyclopentadienylplatinum (IV) compound of formula (2) which is sufficient to convert the irradiation-curable silicone composition to a tack-free state when said composition is subjected to 240–400 nm light.

In still another of its embodiments the present invention comprises a method of coating a substrate with a cured tack-free silicone film, which comprises, (1) applying onto the surface of the substrate to a thickness of about 0.5 to about 5 mil, an irradiation-curable silicone composition comprising, (a) an alkenyl-substituted polydiorganosiloxane having alkenyl radicals attached to silicon by carbon-silicon bonds, where the alkenyl radicals can be in the terminal position, in the polymer backbone, or a combination thereof, (b) a silicon hydride cross-linker, and, (c) an amount of a photo-active cyclopentadienylplatinum (IV) compound of formula (2) which is sufficient to convert the irradiation-curable silicone composition to a tack-free state, and (2) irradiating the surface of the applied irradiation-curable silicone composition with light in the range of 240–400 nm.

In still other of its embodiments the present invention comprises substrates coated with an irradiation-curable silicone composition and the corresponding substrates coated with the subsequently cured silicone film comprising platinum (IV) compounds included within formula (2), and any reaction products thereof which may have been formed, for example, during processing and irradiation-curing.

DETAILED DESCRIPTION OF THE INVENTION

The photo-active cyclopentadienylplatinum (IV) compounds of the present invention are shown by the following formula, $$[(R^1)_a(R^2)_b Cp]Pt(R^3)_3 \qquad (2)$$

where $R^1$ is a $C_{7-20}$ aromatic organic radical, $R^2$ is a $C_{1-22}$ aliphatic organic radical, $R^3$ is a $C_{1-22}$ aliphatic organic radical or a $C_{6-20}$ aromatic organic radical, Cp is a cyclopentadienyl radical, "a" is an integer equal to 1 to 3 inclusive, "b" is an integer equal to 0 to 3 inclusive, and the sum of a +b is equal to 1 to 4 inclusive. In one embodiment the photo-active cyclopentadienylplatinum (IV) compounds of formula (2) can be synthesized by effecting reaction between a $C_{7-20}$ aromatic-substituted cyclopentadienyl compound having the formula, $$(R^1)_a(R^2)_b CpM, \qquad (3)$$

and a platinum (IV) compound having the formula, $$XPt(R^3)_3 \qquad (4)$$

where $R^1$, $R^2$, $R^3$, Cp, "a" and "b" are as previously defined, M is a metallic anion, such as lithium, and X is an anionic leaving group, such as, but not limited to, triflate, borate, phosphate, or halogen.

Among the $C_{7-20}$ aromatic organic radicals shown by $R^1$ of formula (2), there are included tolyl, naphthyl, 2-benzoylnaphthalene, thioxanthone, 2-chlorothioxanthone, 2-isopropylthioxanthone, anthraquinone, 1-chloroanthraquinone, acetophenone, benzophenone, 9,10-dimethylanthracene, 9,10-dichloroanthracene, biphenyl, anthracenyl, phenanthryl and pyrenyl. Further, the cyclopentadienyl compound can be substituted with an $\eta^5$-fluorenyl group. Preferred $C_{7-20}$ aromatic 10 organic radicals are naphthyl, biphenyl, anthracenyl, phenanthryl and pyrenyl.

Aliphatic organic radicals included within both $R^2$ and $R^3$ groups are $C_{1-22}$ aliphatic moieties which can independently be the same or different, and include, but are not limited to, methyl, ethyl, propyl, isopropyl, butyl, allyl, aryl-substituted aliphatic moieties including benzyl and substituted benzyl, and cycloaliphatic groups including cyclopentyl and cyclohexyl. Aromatic organic radicals included within $R^3$ are $C_{6-20}$ aromatic moieties which can be the same or different, and include, but are not limited to, phenyl, and substituted phenyl, particularly alkyl-substituted phenyl. Mixtures of $C_{1-22}$ aliphatic moieties and $C_{6-20}$ aromatic moieties for $R^3$ are also within the scope of the invention. In preferred embodiments both $R^2$ and $R^3$ groups are independently $C_{1-22}$ aliphatic moieties, more preferably independently $CI_{1-12}$ aliphatic moieties, and most preferably independently $C_{1-6}$ aliphatic moieties. In especially preferred embodiments of the present invention $R^2$ and $R^3$ groups are methyl.

Illustrative examples of the compounds of formula (2), include, [1'-naphthyl)-cyclopentadienyl]trimethyl platinum; [2'-naphthyl)-cyclo-pentadienyl]trimethyl platinum; [1-methyl-3-(1'-naphthyl)-cyclopentadienyl]trimethyl platinum; [1-methyl-3-(2'-naphthyl)-cyclopentadienyl]trimethyl platinum; [(4'-biphenyl)-cyclopentadienyl]trimethyl platinum; [1-(4'-biphenyl)-3-methyl-cyclopentadienyl]trimethyl platinum; [9'-phenanthryl)-cyclopentadienyl]-trimethyl platinum; [1-methyl-3-(9'-phenanthryl)-cyclopentadienyl]-trimethyl platinum; [1-(2'-anthracenyl)- 3-methyl-cyclopentadienyl]-trimethyl platinum; [(2'-anthracenyl)-cyclopentadienyl]-trimethyl platinum; [(1'-pyrenyl)-cyclopentadienyl]-trimethyl platinum; and [1-methyl-3-(1'-pyrenyl)-cyclopentadienyl]trimethyl platinum.

The irradiation-curable silicone compositions of the present invention can be made by incorporating an effective amount of a photo-active platinum (IV) compound included within formula (2) into an irradiation-curable silicone blend comprising an alkenyl-substituted polydiorganosiloxane and a silicon hydride cross-linker. An effective amount of the photo-active platinum (IV) compound of formula (2) is an amount sufficient to provide from about 5 ppm to about 500 ppm of platinum, and preferably, about 10 to about 200 ppm based on the weight of irradiation-curable silicone mixture.

If any of the components of the irradiation-curable silicone composition is a solid or is extremely viscous, a solvent can be introduced into the composition to facilitate uniform mixing of the composition components. Suitable solvents include aromatic hydrocarbons, such as, but not limited to, xylene and toluene, aliphatic hydrocarbons, such as, but not limited to, hexane and mineral spirits, halogenated hydrocarbons, such as, but not limited to, dichloromethane, chlorobenzene and trichlorobenzene, and ethers, such as, but not limited to, tetrahydrofuran, methyltetrahydrofuran, and dioxane. From about 0.01 to about 10 parts of solvent per part by weight of the irradiation-curable silicone composition may be used. The resulting composition will generally be sufficiently pure for its intended use. However, it may be desirable to remove the solvent, if one has been employed, by any convenient means known in the art.

As used hereinafter, the expression "irradiation curable" refers to the ability to convert an irradiation-curable silicone composition to a non-smear, tack-free film, after it has been applied in a continuous, semi-continuous, or batch manner onto a substrate, such as a paper substrate, a plastic substrate, or a metal substrate, to a thickness of about 0.5 to about 5 mils.

Lamps which can be used to effect an irradiation cure preferably provide light in the range of about 240 nanometers (nm) to about 400 nm, and most preferably, about 240 nm to about 350 nm. Depending on lamp intensity, which can vary over about 200 watts (W) to about 600 W, a continuous application rate can vary over a line speed of about 50 feet per minute (ft/min) to about 1500 ft/min.

While a variety of irradiation-curable coating compositions are included within the scope of the present invention, a preferred variety of coating compositions are useful in the paper coating art. Accordingly, the alkenyl-containing polydiorganosiloxane, which preferably consists essentially of chemically combined dimethylsiloxy units, can be a polydimethylsiloxane having vinyl radicals attached to silicon. While vinyl radicals can be in the backbone or in the terminal position, vinyl terminated polydimethylsiloxane is particularly preferred. The vinylsiloxy unit content can be about 0.05 to about 3.5 mole percent, and preferably, about 0.14 to about 2 mole percent based on total siloxy units.

While dimethylsiloxy units are preferred, other diorganosiloxy units which can be in the backbone include for example, methylphenylsiloxy units, methyltrifluoropropylsiloxy units, and diphenylsiloxy units.

The alkenyl-containing polydiorganosiloxane can have a viscosity of about 100 centipoise to about 10,000 centipoise at 25° C., and preferably about 150 centipoise to about 600 centipoise.

The silicon hydride cross-linker can be present in the irradiation-curable coating composition at from about 0.1 part to about 10 parts by weight, based on 100 parts by weight of the alkenyl-containing polydiorganosiloxane. The silicon hydride cross-linker can have a viscosity of about 20 to about 1000 centipoise, and preferably about 30 to about 40 centipoise, and can have about 0.04% to about 1.4% by weight of hydrogen attached to silicon.

Another embodiment of the present invention comprises a method of coating a substrate with a cured tack-free silicone film, which comprises, (1) applying onto the surface of the substrate to a thickness of about 0.5 to about 5 mil, an irradiation-curable silicone composition comprising,
  (a) an alkenyl-substituted polydiorganosiloxane having alkenyl radicals attached to silicon by carbon-silicon bonds, where the alkenyl radicals can be in the terminal position, in the polymer backbone, or a combination thereof,
  (b) a silicon hydride cross-linker, and,
  (c) an amount of a photo-active cyclopentadienylplatinum (IV) compound of formula (2) which is sufficient to convert the irradiation-curable silicone composition to a tack-free state, and
(2) irradiating the surface of the applied irradiation-curable silicone composition with light in the range of 240–400 nm.

Still other embodiments of the present invention comprise substrates coated with an irradiation-curable silicone composition and the corresponding substrates coated with the subsequently cured silicone film comprising platinum (IV) compounds included within formula (2), and any reaction products thereof which may have been formed, for example, during processing and irradiation-curing. Suitable substrates which can be coated with a curable silicone composition and subsequently cured silicone film include, but are not limited to, cellulose-based substrates, such as paper, preferably Glassine or super-calendered Kraft paper, and film substrates, such as polyethylene, polypropylene, and polyester, such as Mylar, and hybrid substrates, such as those comprising polyethylene-Kraft paper or polypropylene-Kraft paper. Suitable substrates also include those which are substantially non-porous, such as glass or metal.

In order that those skilled in the art will be better able to practice the invention, the following examples are given by way of illustration and not by way of limitation. All parts are by weight unless otherwise indicated.

EXAMPLE 1

A cyclopentadienylplatinum (IV) compound, as shown by formula (2) was synthesized by initially preparing, as follows, a $C_{7-20}$ aromatic-substituted cyclopentadienyl compound within the scope of formula (3):

There was added 10 milliliters (mL) of dry tetrahydrofuran to a flame-dried flask containing 1.4795 grams (g), (5.7537 millimoles [mmol]) of 9-bromophenanthrene under argon. A pale yellow solution was formed with stirring and it was cooled to −78° C. in a dry ice/acetone bath. There was slowly added dropwise to the yellow solution while it was stirred at −78° C., 12.8 mmol of sec-butyllithium lithium as a 1.185 M solution in cyclohexane. A tan mixture was formed at the end of the addition.

After 12 minutes at −78° C., there was added dropwise to the tan mixture, 0.60 mL (6.06 mmol) of 3-methyl-2-cyclopentene-1-one (dried over molecular sieves). After stirring at 30 minutes at −78° C., the mixture was allowed to warm to room temperature slowly. One hour later, the tan mixture was cooled to 0° C. in an ice bath.

There was slowly added to the tan mixture, 14.4 mmol of a 2.88 M HCl solution. Gas evolution resulted, and a precipitate formed. The reaction was stirred at ambient temperature for 30 minutes; the volume was reduced under reduced pressure to ~4 ml. A viscous orange oily material was obtained which was extracted three times with diethyl ether. The combined ether extracts were washed with distilled water and with aqueous sodium bicarbonate. The resulting orange layer was dried over magnesium sulfate and concentrated under vacuum to 1.37 g of a tacky orange solid.

Inside an argon-filled dry box, the above crude product was dissolved in 3 mL of diethyl ether followed by 40 mL of hexane. There was added, 6.93 mmol of n-butyllithium as a 1.54 M solution in hexane. The mixture was stirred for 1.5 hours, and filtered. There was obtained 742 milligrams (mg) of a tan product after drying under reduced pressure. Based on method of preparation and starting weight of 9-bromophenanthrene, there was obtained a 49% yield of lithium 1-methyl-3-(9'-phenanthryl)cyclopentadienide.

The lithium 1-methyl-3-(9'-phenanthryl) cyclopentadienide salt was then reacted with trimethylplatinum iodide to form a compound within the scope of formula (2) in accordance with the following procedure:

There was added dropwise under anhydrous conditions in the dark, a dry tetrahydrofuran solution of 0.843 mole of lithium 1-methyl-3-(9'-phenanthryl)cyclopentadienide to a vessel containing 0.765 mmol of stirring trimethylplatinum iodide in tetrahydrofuran at 0° C. under argon. The resulting mixture was allowed to stir at room temperature for 75 minutes to form a homogeneous deep orange solution. Volatile materials were separated under reduced pressure to yield a viscous orange oil. The oil was extracted four times with 10 mL of hexane in the dark. The combined extracts were reduced under vacuum to 4 mL. The resulting yellow product was subjected to −30° C. to form crystalline clumps. There was obtained 197 mg (52% yield) of product. Based on method of preparation, NMR spectroscopy and mass spectrometry, the product was [1-methyl-3-(9'-phenanthryl)cyclopentadienyl]trimethylplatinum.

Following a substantially similar procedure, additional cyclopentadienylplatinum (IV) compounds shown by formula (2) were prepared, such as [1-methyl-3-(2'-naphthyl)-cyclopentadienyl]trimethyl platinum, and [1-(4'-biphenyl)-3-methylcyclopentadienyl]trimethyl platinum. The respective platinum compounds were recovered as yellow powders. The naphthyl compound (271 mg) was obtained in 47% yield and the biphenyl compound (260 mg) was obtained in 42% yield.

EXAMPLE 2

A hydrosilylation catalyst evaluation test was run to compare catalytic effectiveness of [1-methyl-3-(9'-phenanthryl)-cyclopentadienyl]trimethylplatinum of Example 1, and a mixture of a commercially available cyclopentadienylplatinum compound, such as $CH_3CpPt(CH_3)_3$, and phenanthrene, as a sensitizer. In evaluating the catalysts, there was used a silicone mixture based on materials obtained from GE Silicone Products Division at Waterford, N.Y. The silicone mixture consisted of 10 parts of SL6100, a vinyl-terminated polydimethylsiloxane having a viscosity of 200 centipoise, and 0.5 part of SL 6020, a siloxane hydride cross-linker having a viscosity of 35 centipoise.

The respective irradiation-curable silicone mixtures were applied onto Glassine® paper with a doctor blade and cured on an RPC UV processor, PPG model 1202, which was fitted with 400–500 W mercury arc lamps. A line speed of 100–200 ft/min was used.

Degree of cure of the coatings was determined by using a smear test and a tape migration test. In the smear test, a 0.5 to 5 mil coating was applied, followed by irradiation. The coating was then rubbed firmly and checked for any smears. In the tape migration test, the adhesive surface of tape was pressed firmly onto a freshly cured coating. The adhesive surface of the tape was then checked for surface migration by folding and self-contacting its adhesive surface to manually determine whether any change occurred in degree of adhesion.

Catalytic effectiveness was measured with respect to achieving a non-smear, no migration cure of the silicone mixture using the respective catalysts. Values such as ppm of Pt, line speed, and lamp intensity, needed to achieve a satisfactory cure were measured.

In evaluating a mixture of $CH_3CpPt(CH_3)_3$, and phenanthrene as a sensitizer, it was found that 1800 ppm is the optimum level of phenanthrene. At higher levels, particularly 10,000 ppm or greater, phenanthrene was found to be incompatible in the silicone mixture. It was found that a non-smear, no migration cure at a line speed of 100 ft/min using a 400W lamp required 200 ppm of Pt and 1800 ppm of phenanthrene based on curable mixture.

On the other hand, a non-smear, no migration cure of the silicone mixture was achieved with [1-methyl-3-(9'-phenanthryl)-cyclopentadienyl]trimethyl platinum of Example 1 in the absence of phenanthrene, at a line speed of 200 ft/min with a 400W lamp, using only 100 ppm of Pt based on the weight of curable mixture.

EXAMPLE 3

A series of irradiation-curable silicone mixtures containing a cyclopentadienylplatinum (IV) compound of Example 1 were respectively evaluated for shelf-life stability at room temperature in the substantial absence of light.

The respective platinum compounds were introduced and mixed vigorously as a toluene solution into a silicone mixture. There was employed sufficient platinum compound to provide 100 ppm of platinum, based on the weight of silicone mixture. The silicone mixture consisted of 95.2 parts of a vinyl-terminated polydimethylsiloxane having a viscosity of 200 centipoise at 25° C., and 4.8 parts of a trimethylsiloxy-terminated polysiloxane consisting essentially of a mixture of methylhydrogensiloxy units and dimethylsiloxy units and having a viscosity of 35 centipoise at 25° C.

In the following table, "Bath Life", measured in the absence of light is the time required for the curable silicone formulation to show a viscosity increase sufficient to interfere with free flow when shaken. In addition, $C_{10}H_7$ is a naphthyl group, $C_{12}H_9$ is a biphenyl group, and $C_{14}H_9$ is a phenanthryl group:

| Catalyst* | Bath Life |
|---|---|
| $CH_3CpPt(CH_3)_3$** | 24–48 hours |
| $C_{10}H_7(CH_3)CpPt(CH_3)_3$ | 96 hours |
| $C_{12}H_9(CH_3)CpPt(CH_3)_3$ | 144 hours |
| $C_{14}H_9(CH_3)CpPt(CH_3)_3$ | 120 hours |

*formulas refer to the compounds named in the above examples
**used as received from Strem Chemical, Inc., Newburyport, MA.

The "Bath Life" values show that the compositions of the present invention have suitable shelf-life stability in the absence of light.

EXAMPLE 4

Additional curable silicone formulations were prepared following the procedure of Example 3, which were used to treat Kraft paper in the absence of light using a Meyer bar rod. The treated paper was then exposed to fluorescent light.

| Catalyst* | Tack Free |
|---|---|
| $CH_3CpPt(CH_3)_3$ | >24 hours |
| $C_{10}H_7CH_3CpPt(CH_3)_3$ | 31 minutes |

*formulas refer to compounds named in the above examples

EXAMPLE 5

In accordance with the procedures of Example 3, additional curable silicone formulations were prepared in the absence of light. Samples consisting of 2–3 mg formulations were added to aluminum pans. Information on cure speed and extent of cure were determined using Photo Differential Scanning Calorimetry using a Perkin-Elmer Photo-DSC system (DSCT+DPA7) with a PEM500 multipower supply. The light source was a 200 watt Hg/Xe lamp. A temperature of 30° C. was maintained during the test procedure. The following results were obtained:

| | Photo-DSC Experiments | |
|---|---|---|
| Catalyst* | ΔH (J/g) | peak time (min) |
| $CH_3CpPt(CH_3)_3$ | −16.7 | 0.39 |
| $C_6H_5(CH_3)CpPt(CH_3)_3$ | −27.7 | 0.38 |
| $C_{12}H_9(CH_3)CpPt(CH_3)_3$ | −30.6 | 0.26 |
| $C_{10}H_7(CH_3)CpPt(CH_3)_3$ | −34.0 | 0.16 |
| $C_{14}H_9(CH_3)CpPt(CR_3)_3$ | −39.2 | 0.19 |

*formulas refer to compounds named above

The above results show that the cyclopentadienylplatinum compounds of the present invention can be used to provide improved catalysts for the irradiation-curable silicone coating compositions of the present inventions.

Although the above examples are directed to only a few of the very many variables which can be used in the practice of the present invention, it should be understood that the present invention is directed to the use of a much broader variety of cyclopentadienyl-platinum (IV) compounds and the use of such compounds as catalysts in a wide variety of irradiation-curable silicon mixtures as set forth in the description preceding these examples.

What is claimed is:

1. An irradiation-curable silicone composition comprising,
   (a) an alkenyl-substituted polydiorganosiloxane having alkenyl radicals attached to silicon by carbon-silicon bonds, where the alkenyl radicals can be in the terminal position, in the polymer backbone, or a combination thereof,
   (b) a silicon hydride cross-linker, and,
   (c) an effective amount of a photo-active cyclopentadienylplatinum (IV) compound of the formula,

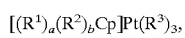

which is sufficient to convert the irradiation-curable silicone composition to a tack-free state when said composition is subjected to 240–400 nm light, where $R^1$ is a $C_{7-20}$ aromatic organic radical, $R^2$ and $R^3$ are each independently a $C_{1-22}$ aliphatic organic radical, Cp is a cyclopentadienyl radical, "a" is an integer equal to 1 to 3 inclusive, "b" is an integer equal to 0 to 3 inclusive, and the sum of a+b is equal to 1 to 4 inclusive.

2. An irradiation-curable silicone composition in accordance with claim 1, where the photo-active cyclopentadienyl-Pt(IV) compound is [1-methyl-3-(9'-phenanthryl)-cyclopentadienyl]trimethyl platinum.

3. An irradiation-curable silicone composition in accordance with claim 1, where the photo-active cyclopentadienyl-Pt(IV) compound is [1-methyl-3-(2'-naphthyl)cyclopentadienyl]trimethyl platinum.

4. An irradiation-curable silicone composition consisting essentially of,
   (d) an alkenyl-substituted polydiorganosiloxane having alkenyl radicals attached to silicon by carbon-silicon bonds, where the alkenyl radicals can be in the terminal position, in the polymer backbone, or a combination thereof,
   (e) a silicon hydride cross-linker, and,
   (f) an effective amount of a photo-active cyclopentadienylplatinum (IV) compound selected from the group consisting of [1-methyl-3-(9'-phenanthryl)cyclopentadienyl]trimethyl platinum and [1-methyl-3-(2'-naphthyl)cyclopentadienyl]trimethyl platinum, which is sufficient to convert the irradiation-curable silicone composition to a tack-free state when said composition is subjected to 240–400 nm light.

5. A method of coating a substrate with a cured tack-free silicone film, which comprises,
   (1) applying onto the surface of the substrate to a thickness of about 0.5 to about 5 mil, an irradiation-curable silicone composition comprising,
      (a) an alkenyl-substituted polydiorganosiloxane having alkenyl radicals attached to silicon by carbon-silicon bonds, where the alkenyl radicals can be in the terminal position, in the polymer backbone, or a combination thereof,
      (b) a silicon hydride cross-linker, and,
      (c) an amount of a photo-active cyclopentadienylplatinum (IV) compound of the formula,

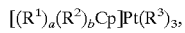

which is sufficient to convert the irradiation-curable silicone composition to a tack-free state, and
   (2) irradiating the surface of the applied irradiation-curable silicone composition with light in the range of 240–400 nm, where $R^1$ is a $C_{7-20}$ aromatic organic radical, $R^2$ and $R^3$ are each independently a $C_{1-22}$ aliphatic organic radical, Cp is a cyclopentadienyl radical, "a" is an integer equal to 1 to 3 inclusive, "b" is an integer equal to 0 to 3 inclusive, and the sum of a+b is equal to 1 to 4 inclusive.

6. A coating method in accordance with claim 5, where the photo-active cyclopentadienylplatinum (IV) compound is [1-methyl-3-(9'-phenanthryl)cyclopentadienyl]trimethyl platinum.

7. A coating method in accordance with claim 5, where the substrate is cellulose-based.

8. A substrate coated with an irradiation-curable silicone composition comprising, a platinum (IV) compound having the formula,

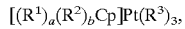

and any reaction products thereof, where $R^1$ is a $C_{7-20}$ aromatic organic radical, $R^2$ and $R^3$ are each independently a $C_{1-22}$ aliphatic organic radical, Cp is a cyclopentadienyl radical, "a" is an integer equal to 1 to 3 inclusive, "b" is an integer equal to 0 to 3 inclusive, and the sum of a+b is equal to 1 to 4 inclusive.

9. A substrate according to claim 8, in which the silicone coating composition has been irradiation-cured.

10. A substrate according to claim 8, which is cellulose-based.

11. A substrate according to claim 10, in which the silicone coating composition has been irradiation-cured.

* * * * *